United States Patent
Hong et al.

(10) Patent No.: US 10,882,882 B2
(45) Date of Patent: Jan. 5, 2021

(54) POST FERMENTED TEA-DERIVED KAEMPFEROL-BASED COMPOUND

(71) Applicant: AMOREPACIFIC CORPORATION, Seoul (KR)

(72) Inventors: Yong-Deog Hong, Yongin-si (KR); Minsik Choi, Yongin-si (KR); Si Young Cho, Yongin-si (KR); Jeong-Kee Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/340,920

(22) PCT Filed: Oct. 12, 2017

(86) PCT No.: PCT/KR2017/011250
§ 371 (c)(1),
(2) Date: Apr. 10, 2019

(87) PCT Pub. No.: WO2018/074776
PCT Pub. Date: Apr. 26, 2018

(65) Prior Publication Data
US 2019/0284223 A1 Sep. 19, 2019

(30) Foreign Application Priority Data
Oct. 18, 2016 (KR) .................. 10-2016-0135301

(51) Int. Cl.
C12P 19/60 (2006.01)
C07H 17/07 (2006.01)
A61K 31/7048 (2006.01)
A61K 36/82 (2006.01)

(52) U.S. Cl.
CPC ......... *C07H 17/07* (2013.01); *A61K 31/7048* (2013.01); *A61K 36/82* (2013.01); *C12P 19/60* (2013.01)

(58) Field of Classification Search
CPC ...................................................... C12P 19/60
See application file for complete search history.

(56) References Cited

FOREIGN PATENT DOCUMENTS

WO 2018074776 A1 4/2018

OTHER PUBLICATIONS

Tang et al., Phytochemistry, 2001, 58, p. 1251-1256. (Year: 2001).*
Zhao et al., Food Chemistry, 2011, 126, p. 1269-1277. (Year: 2011).*
Lv et al., Food Research International, 2013, 53, p. 608-618. (Year: 2013).*
Lu-Rong Xu, et al., "A new acylated flavonol glycoside from Derris triofoliata", Journal of Asian Natural Products Research,vol. 8, No. 1-2, Jan.-Mar. 2006, 9-13
G. W. Plumb, et al., "Antioxidant properties of flavonol glycosides from tea", Redox Report, vol. 4, No. 1/2, 1999.
International Search Report for International Application No. PCT/KR2017/011250, International Filing Date Oct. 12, 2017, dated Jan. 22, 2018, 6 pages.
Md. Maniruzzaman Manir, et al., "Tea catechins and flavonoids from the leaves of Camellia sinensis inhibit yeast alcohol dehydrogenase", Bioorganic & Medicinal Chemistry 20 (2012) 2376-2381.
Sheng-Kuo Hsieh, et al., "Identification of biosynthetic intermediates of teaghrelins and teaghrelin-like compounds in oolong teas, and their molecular docking to theghrelin receptor", Journal of Food and Drug Analysis 23 (2015) 660-670.
Xi-Feng Teng, et al., "Five New Flavonol Glycosides from the Fresh Flowers of Camellia reticulata", Helvetica Chimica Acta—vol. 91 (2008).

* cited by examiner

*Primary Examiner* — Jonathan S Lau
(74) *Attorney, Agent, or Firm* — Cantor Colburn LLP

(57) ABSTRACT

The present specification relates to a novel compound separated from post fermented tea, an isomer thereof, a pharmaceutically acceptable salt thereof, a hydrate thereof, or a solvate thereof, the compound being capable of being widely used in post fermented tea-related industries and various fields in which the compound may be used.

5 Claims, 6 Drawing Sheets

POST FERMENTED TEA-DERIVED KAEMPFEROL-BASED COMPOUND

This application is a national stage application of PCT/KR2017/011250, filed Oct. 12, 2017, which claims priority to KR 10-2016-0135301, filed Oct. 18, 2016 both of which are hereby incorporated by reference in their entirety.

TECHNICAL FIELD

The present specification relates to a novel post fermented tea-derived kaempferol-based compound.

BACKGROUND ART

Green tea is consumed as a coarse tea in the leaf form or as a fermented tea to feel deeper flavor. Fermented green tea means one obtained by subjecting green tea leaves to oxidation treatment and includes fermented tea oxidized using oxidizing enzymes present in the tea leaves and post fermented tea fermented using microorganisms other than the enzymes present in the tea leaves. Fermented green tea can be divided into weak fermented tea, semi-fermented tea, and fully fermented tea depending on the degree of fermentation. For example, fermented green tea is called various names such as green tea, oolong tea, black tea, and pu'er tea depending on the type and degree of fermentation.

China and Japan have the manufacturing technology of post fermented tea in the world. In the aerobic fermented tea of China, fungi are used as fermentation strains, and the main producing district thereof is Xishuangbanna Autonomous prefecture of Yunnan province. In the aerobic fermented tea of Japan, fungi are used as fermentation strains, and Toyama is a major producing district of black tea. In the anaerobic fermented tea, anaerobic lactobacilli are used as fermentation strains, and the main producing district thereof is Awa. In addition, there is black tea, in which anaerobic fungi are used as fermentation strains and the main producing district of which is Ishizuchi. In the case of the traditional pu'er tea which originated in Pu'er prefecture of China, green tea leaves are deliberately hurt when being collected, and the green tea leaves are heated and roasted, then an appropriate amount of water is added thereto, and the green tea leaves are subjected to natural fermentation using microorganisms in the air. In Korea, fermented tea is produced and consumed intermittently in the form of domestic handicrafts in Jirisan and Boryeong.

Fermented tea may have not only a difference in flavor compared to coarse tea but also a great difference in the kind and content of active ingredient depending on the specific fermentation process and the kind of microorganisms. Since various compounds can be produced and separated from green tea as described above, a variety of attempts have been made to separate and identify unknown novel compounds using green tea.

Meanwhile, kaempferol is one of flavonoids and is known to exist in the form of secondary metabolites in a variety of plants in nature.

SUMMARY OF INVENTION

Technical Problem

In an aspect, an object of the present invention is to discover a novel compound from a post fermented tea and to industrially utilize this.

In another aspect, an object of the present invention is to provide a method for manufacturing the novel compound and thus to enhance the industrial applicability of the novel compound.

Solution to Problem

In order to solve to above problems, in an aspect, the present invention provides a compound represented by the following Chemical Formula 1, an isomer thereof, a pharmaceutically acceptable salt thereof, a hydrate thereof, or a solvate thereof.

[Chem. 1]

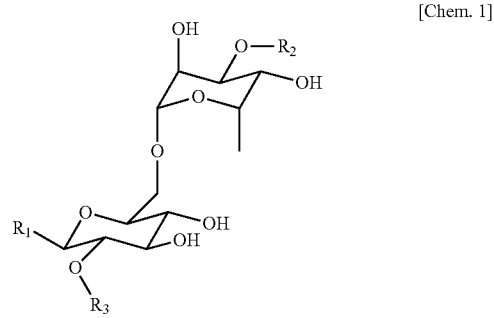

where $R_1$ may represent $C_{15}H_9O_6$, $R_2$ may represent $C_6H_{11}O_5$, and $R_3$ may represent $C_9H_7O_2$.

In another aspect, the present invention also provides a method for manufacturing the compound, an isomer thereof, a pharmaceutically acceptable salt thereof, a hydrate thereof, or a solvate thereof.

Advantageous Effects of Invention

In an aspect of the present invention, by separating a novel compound from post fermented tea and industrially utilizing this, the compound can be widely used in post fermented tea-related industries and various fields in which the compound may be used, and can meet the demands of related consumers.

DESCRIPTION OF EMBODIMENTS

Figure 1:
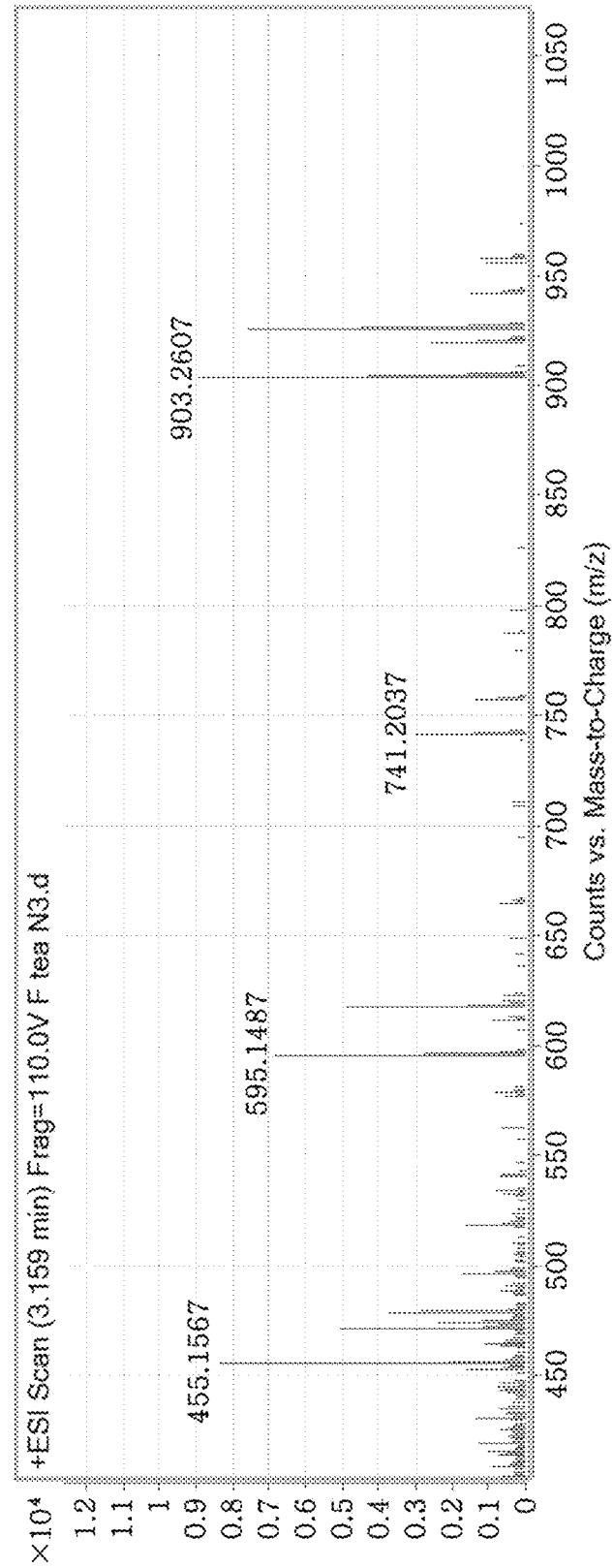
FIG. 1 illustrates the MS spectrum of a compound according to an aspect of the present invention.

In the present specification, "post fermentation" includes fermentation using microorganisms or a substance other than the enzymes present in tea leaves. Post fermented tea includes the green tea fermented by the above-mentioned method.

In the present specification, "fraction" includes fractions obtained by fractionating a specific substance or extract using a certain solvent, remnants, and those obtained by extracting these again using a specific solvent. The fractionation method and the extraction method may be any methods known to those skilled in the art.

In the present specification, "isomers" particularly includes not only optical isomers (e.g., essentially pure enantiomers, essentially pure diastereomers, or mixtures thereof) but also conformation isomers (i.e., isomers different only in the angle of one or more chemical bonds), position isomers (particularly tautomers), or geometric isomers (e.g., cis-trans isomers).

In the present specification, "essentially pure" means that a specific compound having enantiomers or diastereomers is present at about 90% or more, preferably about 95% or more, more preferably about 97% or more or about 98% or more, even more preferably about 99% or more, yet more preferably about 99.5% or more (w/w) in the case of being used in connection with, for example, enantiomers or diastereomers.

In the present specification, "pharmaceutically acceptable" means it is recognized that one can be used for an animal, more specifically humans by avoiding significant toxic effects when being used in conventional medicinal dosages as being capable of being approved or as being approved by the government or a regulatory agency equivalent thereto or as being enumerated in the pharmacopeia or as being described in other general pharmacopeias.

In the present specification, "pharmaceutically acceptable salt" means a salt according to an aspect of the present invention which is pharmaceutically acceptable and has the desired pharmacological activity of the parent compound. The salt may include (1) acid addition salts formed using inorganic acids such as hydrochloric acid, hydrobromic acid, sulfuric acid, nitric acid, and phosphoric acid; or organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-en-1-carboxylic acid, glucoheptonic acid, 3-phenylpropionic acid, trimethylacetic acid, tert-butylacetic acid, laurylsulfuric acid, gluconic acid, glutamic acid, hydroxynaphthoic acid, salicylic acid, stearic acid, and muconic acid; or (2) a salt formed when an acidic proton present in a parent compound is substituted.

In the present specification, "hydrate" means a compound bonded with water and is a broad concept that includes an inclusion compound in which water and the compound do not have chemical bonding force therebetween.

In the present specification, "solvate" means a higher order compound formed between a molecule or ion of a solute and a molecule or ion of a solvent.

In an aspect, the present invention provides a compound represented by the following Chemical Formula 1, an isomer thereof, a pharmaceutically acceptable salt thereof, a hydrate thereof, or a solvate thereof.

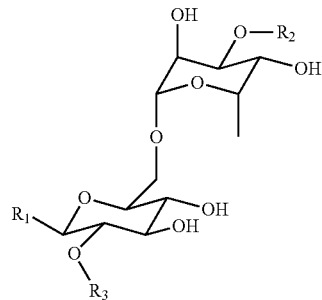

[Chem. 1]

where $R_1$ may represent $C_{15}H_9O_6$, $R_2$ may represent $C_6H_{11}O_5$, and $R_3$ may represent $C_9H_7O_2$.

According to an embodiment, $R_1$ may be a compound represented by the following Chemical Formula 2.

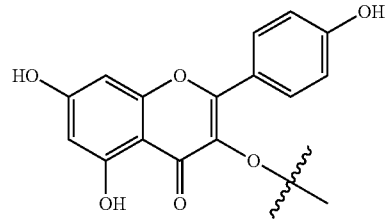

[Chem. 2]

According to another embodiment, $R_2$ may be a compound represented by the following Chemical Formula 3.

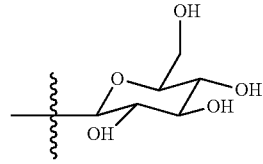

[Chem. 3]

$R_3$ may be a compound represented by the following Chemical Formula 4.

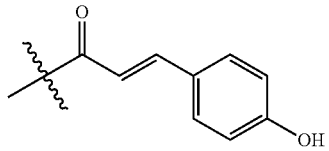

[Chem. 4]

According to another embodiment, the compound may be kaempferol3-O-[2-O"-(E)-p-coumaroyl][beta-D-glucopyranosyl-(1→3)-O-alpha-L-rhamnopyranosyl-(1→6)-O-beta-D-glucopyranoside]. The compound can be represented by the following chemical formula.

[Chem. 5]

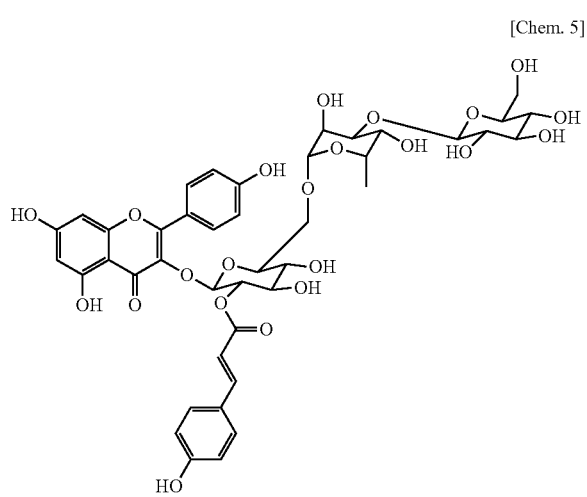 [SMILES: CC1OC(OCC2OC(Oc3c(-c4ccc(O)cc4)oc4cc(O)cc(O)c4c3=O)C(OC(=O)/C=C/c3ccc(O)cc3)C(O)C2O)C(O)C(OC2OC(CO)C(O)C(O)C2O)C1O]

In an aspect of the present invention, the compound is an unknown novel substance, and the present inventors have discovered and separated the novel substance as a result of continuous researches on the post fermented tea. The compound according to an aspect of the present invention exhibits usefulness of inhibiting beta amyloid aggregation (see FIG. 6). Since the beta amyloid aggregation and the like are properties clinically applicable in the field of medicine and fields related thereto, it is thus clear that the compound can be industrially used. It is expected that the compound can be utilized in a variety of industrial fields when the usefulness thereof is further researched.

According to an embodiment, the content of the compound may be 0.01 wt % or more, 0.05 wt % or more, 0.1 wt % or more, 0.2 wt % or more, 0.3 wt % or more, 0.4 wt % or more, 0.5 wt % or more, 0.7 wt % or more, 0.9 wt % or more, 1.0 wt % or more, 1.3 wt % or more, 1.5 wt % or more, 1.7 wt % or more, 2.0 wt % or more, 2.2 wt % or more, 2.5 wt % or more, 2.8 wt % or more, 3.0 wt % or more, 3.3 wt % or more, 3.5 wt % or more, 3.8 wt % or more, 4.0 wt % or more, 4.5 wt % or more, 5.0 wt % or more, 5.5 wt % or more, 6.0 wt % or more, 8.0 wt % or more, 10 wt % or more, 12 wt % or more, 15 wt % or more, or 20 wt % or more based on the total weight of a composition containing this. In addition, the content of the compound may be 18 wt % or less, 15 wt % or less, 12 wt % or less, 10 wt % or less, 8.0 wt % or less, 6.0 wt % or less, 5.5 wt % or less, 5.0 wt % or less, 4.5 wt % or less, 4.0 wt % or less, 3.8 wt % or less, 3.5 wt % or less, 3.3 wt % or less, 3.0 wt % or less, 2.8 wt % or less, 2.5 wt % or less, 2.2 wt % or less, 2.0 wt % or less, 1.7 wt % or less, 1.5 wt % or less, 1.3 wt % or less, 1.0 wt % or less, 0.9 wt % or less, 0.8 wt % or less, 0.7 wt % or less, 0.5 wt % or less, 0.4 wt % or less, 0.3 wt % or less, 0.2 wt % or less, 0.1 wt % or less, 0.05 wt % or less, or 0.03 wt % or less based on the total weight of a composition containing this.

In another aspect, the present invention provides a method for manufacturing the compound, an isomer thereof, a pharmaceutically acceptable salt thereof, a hydrate thereof, or a solvate thereof. The manufacturing method may include synthesis, separation from natural products, and the like.

According to an embodiment, the manufacturing method may be to ferment green tea and then to separate the compound from the fermented green tea. The manufacturing method may include a step of inoculating green tea leaves with fermentation organisms, fermenting the green tea leaves inoculated, drying the green tea leaves fermented using hot air, and then aging the green tea leaves dried and a step of separating the compound from the green tea leaves aged by extraction and fractionation after aging.

The extraction and fractionation may be conducted using water, an organic solvent and the like, and any method known to those skilled in the art is applicable.

According to another aspect, the fractionation may be conducted after the extraction, may be conducted using a ketone, may be conducted by extracting one fractionated using a ketone again using an alcohol (e.g., ethanol).

The ketone may include acetone, carvone, pulegone, isolongifolanone, 2-heptanone, 2-pentanone, 3-hexanone, 3-heptanone, 4-heptanone, 2-octanone, 3-octanone, 2-nonanone, 3-nonanone, 2-undecanone, 2-tridecanone, methyl isopropyl ketone, ethyl isoamyl ketone, butylidene acetone, methyl heptenone, dimethyl octenone, geranyl acetone, farnesyl acetone, 2,3-pentadione, 2,3-hexadione, 3,4-hexadione, 2,3-heptadione, amyl cyclopentanone, amyl cyclopentenone, 2-cyclopentyl cyclopentanone, hexyl cyclopentanone, 2-n-heptyl cyclopentanone, cis-jasmone, dihydrojasmone, methyl corylone, 2-tert-butyl cyclohexanone, p-tert-butyl cyclohexanone, 2-sec-butyl cyclohexanone, celery ketone, krypton, p-tert-pentyl cyclohexanone, methyl cyclocitrone, nerone, 4-cyclohexyl-4-methyl-2-pentanone, oxide ketone, emoxyfurone, methylnaphthyl ketone, α-methyl anisalacetone (1-(4-Methoxyphenyl)-4-methyl-1-penten-3-on 1-(4-Methoxyphenyl)-4-methyl-1-penten-3-one), anisyl acetone, p-methoxyphenyl acetate, benzylidene acetone, p-methoxyacetophenone, p-methylacetophenone, propiophenone, acetophenone, α-dynascone, iritone, ionone, pseudoionone, methyl ionone, methyl iritone, 2,4-di-tert-butyl cyclohexanone, allyl ionone, 2-acetyl-3,3-dimethyl norbornane, verbenone, fenchone, cyclopentadecanone, cyclohexadecenone, and the like. The ketone may include all of ketones as solvents to be commonly used in the art and mixtures thereof, and the ketone may be preferably acetone.

According to another embodiment, the fermentation may be conducted by a post fermentation method. The post fermentation may be conducted by strain inoculation. The strain may be a strain selected from *Saccharomyces* sp., *Bacillus* sp. *Lactobacillus* sp., or *Leuconostoc mesenteroides* sp. and may be preferably selected from *Saccharomyces cerevisiae, Lactobacillus casei, Bacillus subtilis, Lactobacillus bulgarius,* or *Leuconostoc mesenteroides*.

EXAMPLES

Hereinafter, the configuration and effects of the present specification will be described in more detail with reference to Examples and Experimental Examples. However, these examples are provided for illustrative purposes only in order to facilitate understanding of the present specification, and the scope and range of the present specification are not limited by the following examples.

[Example 1] Preparation of Post Fermented Tea Sample

Water was added to green tea made of green tea (*Camellia sinensis* var. *Yabukita*) leaves, and the water content was adjusted to 40 wt %. The green tea was inoculated with *Bacillus subtillis* at $5 \times 10^6$ cfu/g, fermented at 50° C. for 3 days, and then fermented at 80° C. for 4 days.

The aged tea sample was pulverized for 15 seconds and then sieved using a stainless steel sieve having a mesh size of 1 mm. Thereafter, 50 mg of the pulverized tea sample was placed in a 1.5 ml Eppendorf tube, 1 ml of deionized water was added thereto, and the mixture was stirred at a constant speed for 30 minutes in a constant temperature water bath at 60° C. and then centrifuged at 25° C. and 13,000 rpm for 15 minutes. Only the portion which was not soluble in water was separated from the fermented green tea extract dried.

[Example 2] Obtaining of Fraction and Separation of Compound

Catechin derivatives and caffeine were removed by fractionating 150 g of the post fermented tea sample using acetone, and a soluble in which other compounds were concentrated was obtained. By silica gel column chromatography, 40 g of the acetone soluble was first fractionated using a 5:1 (v/v) mixture of chloroform:methanol as a solvent.

By high-performance countercurrent chromatography (HPCCC, Dynamic Extractions Ltd, UK), 8.9 g of the caffeine-free 5:1 (v/v) fraction of chloroform:methanol was fractionated. The solvent used at this time was n-hexane-TBME (methyl tert-butyl ether)-BuOH-MeCN-Water (0.25:3:1:1:5, v/v), and the flow rate was set to 25 ml/min. Under the above conditions, 10 subfractions were obtained in total, and the components contained in each fraction were separated by small-capacity HPCCC (Dynamic Extractions Ltd, UK), HPLC (high-performance liquid chromatography), Sephadex LH-20 column (GE Healthcare Bio-Sciences, Sweden), and the like.

As a result, it was possible to separate kaempferol3-O-[2-O"-(E)-p-coumaroyl][beta-D-glucopyranosyl-(1→3)-O-alpha-L-rhamnopyranosyl-(1→6)-O-beta-D-glucopyranoside], which was a compound unknown in the prior art, from the fractions, and the structure of each compound was identified by $^1$H and $^{13}$C-NMR (nuclear magnetic resonance spectroscopy), UV (ultraviolet spectroscopy), and ESI-MS (electro spray ionization mass spectroscopy). In the case of $^1$H and $^{13}$C nuclear magnetic resonance (NMR), methanol-d3 was used as a solvent and Bruker Advance DPX-500 (BRUKER, USA) was used as an instrument. The MS spectrum of each compound was attained using 6200 Series Accurate-Mass Time-of-Flight (TOF) LC/MS (Agilent, US).

As a result of the analysis, each of the above compounds has been confirmed to be kaempferol3-O-[2-O"-(E)-p-coumaroyl][beta-D-glucopyranosyl-(1→3)-O-alpha-L-rhamnopyranosyl-(1→6)-O-beta-D-glucopyranoside] which has a molecular formula of $C_{42}H_{46}O_{22}$ and a molecular weight of 902.2481 and is a novel compound unknown in the prior art.

The chemical formula and NMR data of kaempferol3-O-[2-O"-(E)-p-coumaroyl][beta-D-glucopyranosyl-(1→3)-O-alpha-L-rhamnopyranosyl-(1→6)-O-beta-D-glucopyranoside] are as follows.

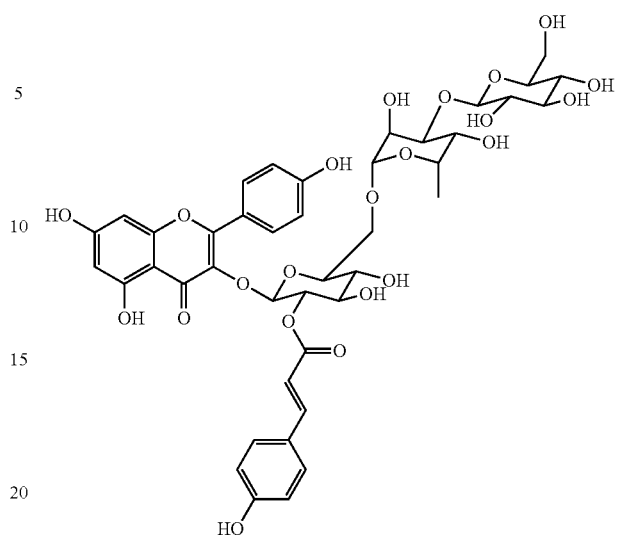

TABLE 1

| Position | $^{13}$C-NMR | $^1$H-NMR |
|---|---|---|
| 2 | 161.26 | |
| 3 | 135.07 | |
| 4 | 179.31 | |
| 5 | 161.5 | |
| 6 | 99.87 | 6.17 (H6, brs) |
| 7 | 165.74 | |
| 8 | 94.8 | 6.35 (H8, brs) |
| 9 | 158.58 | |
| 10 | 105.84 | |
| 1' | 122.72 | |
| 2', 6' | 132.29 | 7.99 (H2'/H6', d, J = 8.3 Hz) |
| 3', 5' | 116.27 | 6.87 (H3'/H5', d, J = 8.3 Hz) |
| 4' | 158.69 | |
| p-coumaric acid | | |
| 1''' | 127.3 | 7.45 (H2'''/H6''', d, J = 8.1 Hz) |
| 2''', 6''' | 131.2 | |
| 3''', 5''' | 116.82 | 6.80 (H3'''/H5''', d, J = 8.1 Hz) |
| 4''' | 161.26 | |
| 7''' | 115.31 | 6.35 (H7''', d, J = 15.7 Hz) |
| 8''' | 146.88 | 7.67 (H8''', d, J = 15.7 Hz) |
| C=O | 168.79 | |
| Glc1 | | |
| 1'' | 101.55 | 5.46 (H1'', d, J = 7.8 Hz) |
| 2'' | 74.14 | 5.34 (H2'', t, J = 9 Hz) |
| 3'' | 73.25 | 3.76 (H3'', d, J = 10.4 Hz) |
| 4'' | 70.47 | 3.85 (H4'', m) |
| 5'' | 75.51 | 3.73 (H5'', m) |
| 6'' | 67.54 | 3.76 (H6'', brd, J = 10.4 Hz) |
| | | 3.54 (H6'', m) |
| Rha | | |
| 1'''' | 101.85 | 4.60 (H1'''', brs) |
| 2'''' | 71.34 | 3.95 (2'''', m) |
| 3'''' | 83.09 | 3.61 (H3'''', dd, J = 9, 3 Hz) |
| 4'''' | 72.6 | 3.46 (H4'''', m) |
| 5'''' | 69.49 | 3.54 (H5'''', m) |
| 6'''' | 18.08 | 1.19 (H'''', d, J = 6 Hz) |
| Glc2 | | |
| 1''''' | 105.74 | 4.40 (H1''''', d, J = 7.5 Hz) |
| 2''''' | 75.4 | 3.25 (H2''''', m) |
| 3''''' | 77.6 | 3.36 (H3''''', m) |
| 4''''' | 70.84 | 3.36 (H4''''', m) |
| 5''''' | 77.6 | 3.25 (H5''''', m) |
| 6''''' | 62.05 | 3.71 (H6''''', m) |

Figure 2:
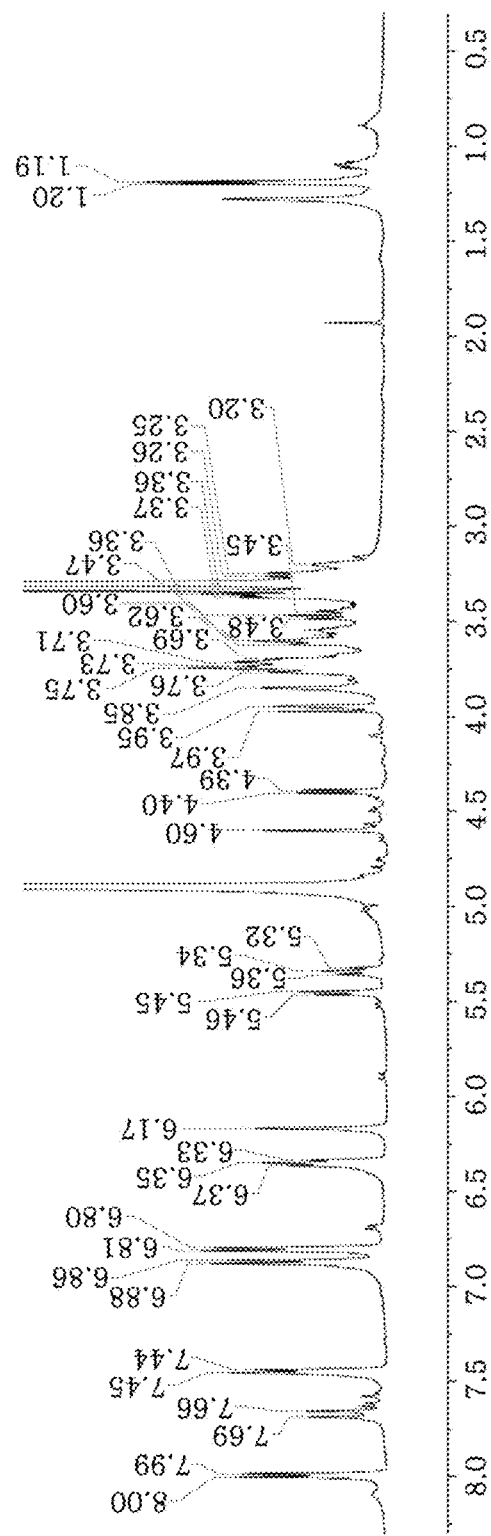
FIG. 2 illustrates the $^1$H-NMR (nuclear magnetic resonance) spectrum of a compound according to an aspect of the present invention.
Figure 3:
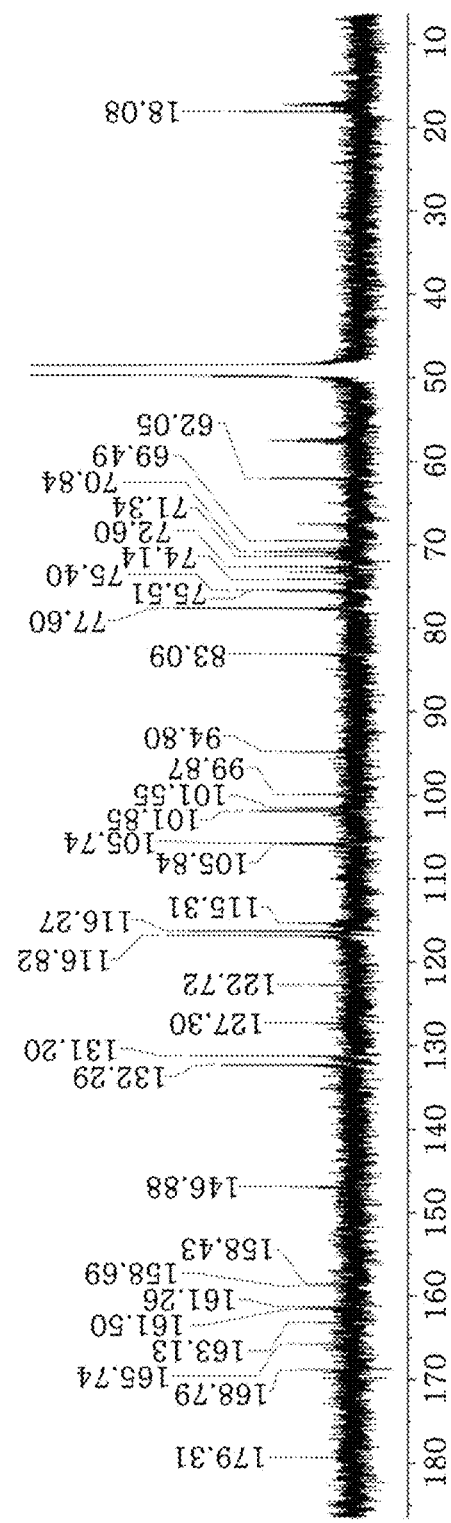
FIG. 3 illustrates the $^{13}$C-NMR spectrum of a compound according to an aspect of the present invention.
Figure 4:
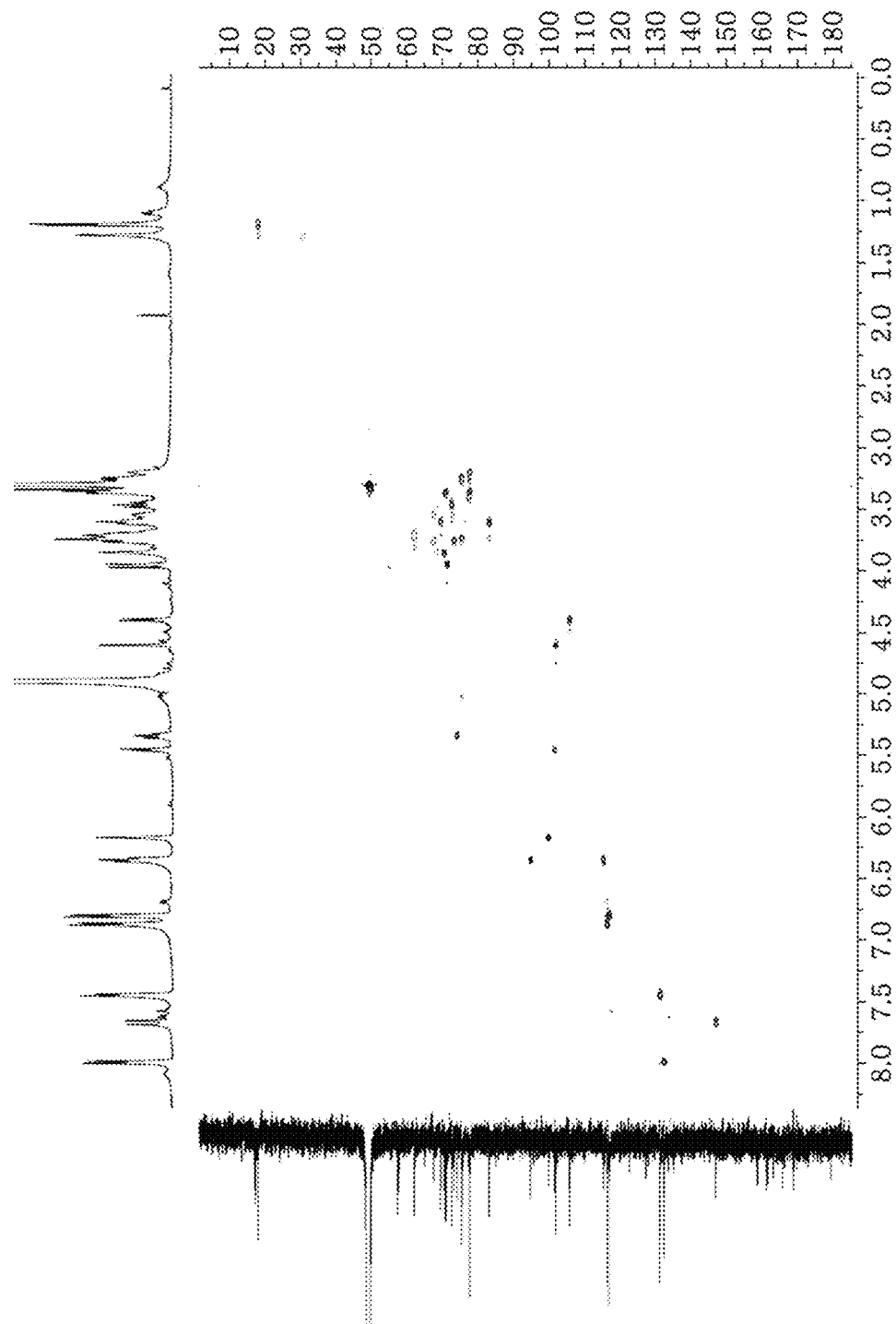
FIG. 4 illustrates the $^1$H-$^{13}$C HSQC (heteronuclear single quantum coherence) spectrum of a compound according to an aspect of the present invention.
Figure 5:
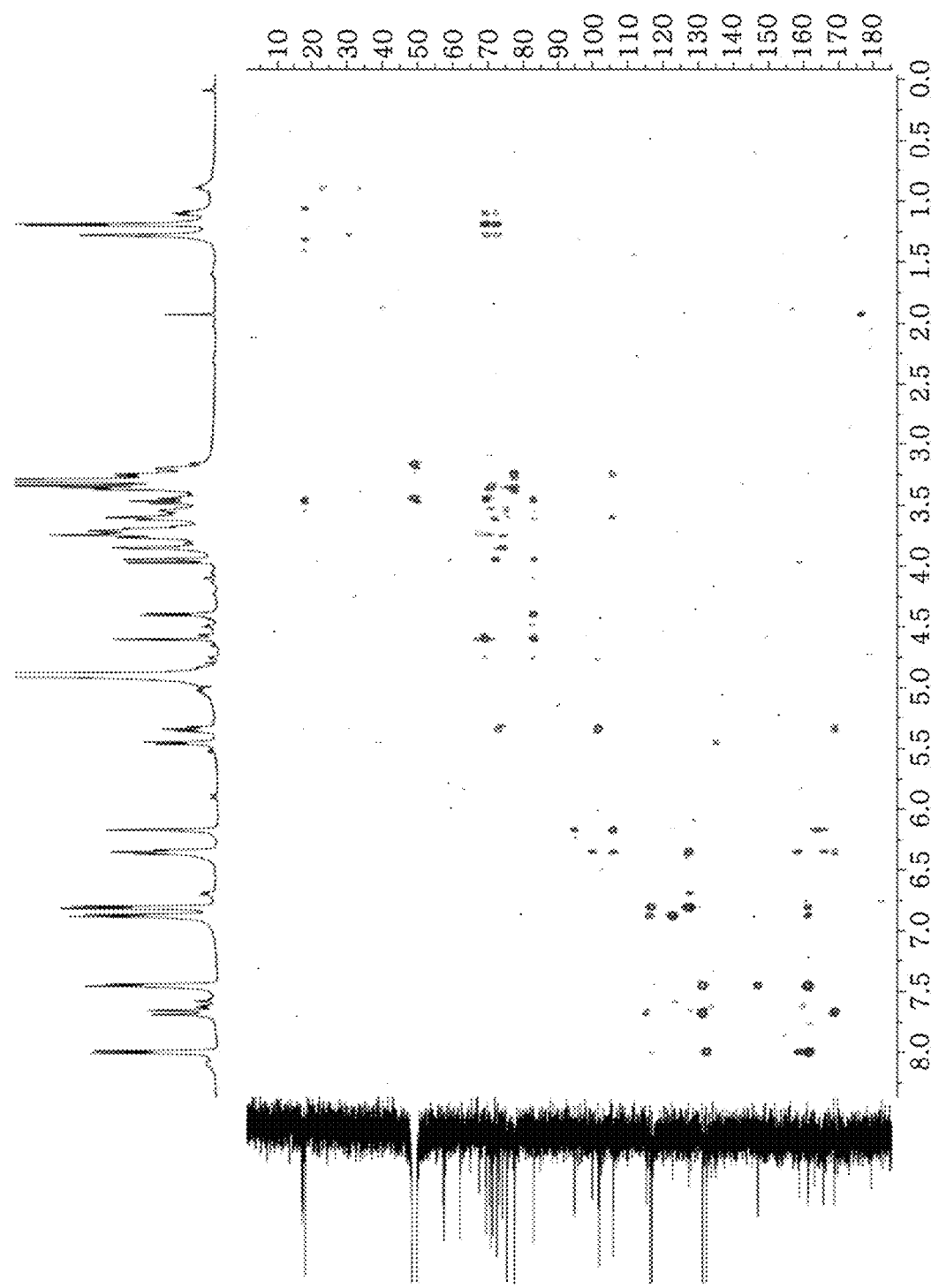
FIG. 5 illustrates the $^1$H-$^{13}$C HMBC (heteronuclear multiple-bond coherence) spectrum of a compound according to an aspect of the present invention.

The MS spectrum of kaempferol3-O-[2-O"-(E)-p-coumaroyl][beta-D-glucopyranosyl-(1→3)-O-alpha-L-rhamnopyranosyl-(1→6)-O-beta-D-glucopyranoside] is as illustrated in FIG. 1, and the $^1$H-NMR spectrum and $^{13}$C-NMR spectrum thereof are as illustrated in FIG. 2 and FIG. 3, respectively, the HSQC (heteronuclear single quantum coherence) spectrum thereof is as illustrated in FIG. 4, and the HMBC (heteronuclear multiple-bond coherence) spectrum thereof is as illustrated in FIG. 5.

[Experimental Example 1] Experiment on Effect of Inhibiting Beta Amyloid Aggregation The effect of kaempferol3-O-[2-O"-(E)-p-coumaroyl][beta-D-glucopyranosyl-(1→3)-O-alpha-L-rhamnopyranosyl-(1→6)-O-beta-D-glucopyranoside] on inhibition of beta amyloid aggregation was confirmed by the fluorescence analysis (ThioflavinT assay).

Specifically, beta amyloid (Aβ1-42, AnaSpec Inc, USA) was obtained and used at a concentration of 0.1 mg/ml and stored at −80° C. before use. Morin (20 μM), phenol red (20 μM), and kaempferol3-O-[2-O"-(E)-p-coumaroyl][beta-D-glucopyranosyl-(1→3)-O-alpha-L-rhamnopyranosyl-(1→6)-O-beta-D-glucopyranoside] (1 mg/ml) were respectively diluted with DMSO so as to be adjusted to the concentrations.

In order to specify the degree of inhibition of Aβ1-42 aggregation, each of the compounds prepared at the above concentrations was diluted with 50 μL of 0.01 M sodium phosphate buffer solution to have a concentration of 10 μM, then 40 μL of 0.1 mg/ml of Aβ1-42 was added thereto, and then 10 μl of 2 mM thioflavinT was added thereto, and fluorescence was measured using a fluorescence spectrometer (RF-5300PC, SHIMADZU CORPORATION, Japan) at 37° C. for 150 minutes at intervals of 5 minutes.

Figure 6:
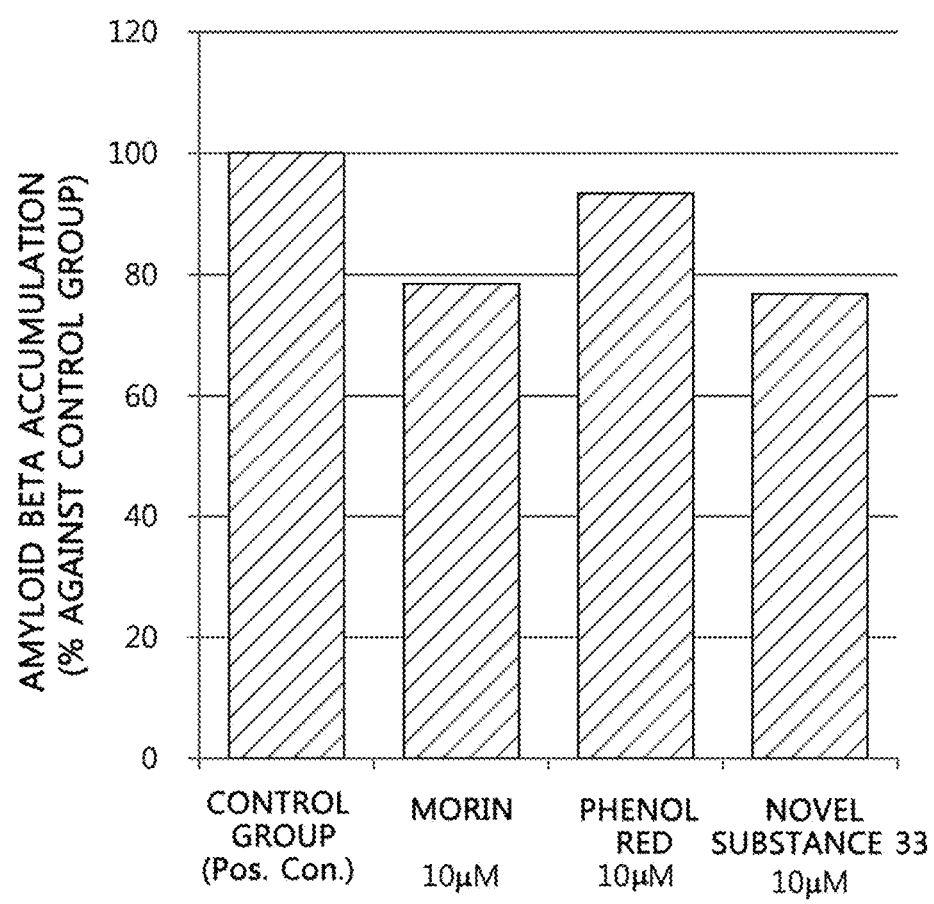
FIG. 6 illustrates the influence of a compound according to an aspect of the present invention on beta amyloid aggregation.

The results are as presented in the following Table 2 and FIG. 6.

TABLE 2

| | Increased RFU | Increased RFU (% of Pos. Cont.) |
|---|---|---|
| Pos. Cont. | 14595 | 100.0 |
| Novel substance 33 | 11235 | 77.0 |
| Morin | 11471 | 78.6 |
| Phenol Red | 13655 | 93.6 |

In the above table, "RFU" denotes the relative fluorescence unit, and "Increased RFU" denotes the amount of aggregated beta amyloid, and "Increased RFU (% of Pos.Cont.)" denotes the percentage value of the amount of aggregated beta amyloid with respect to that of the positive control group. "Novel substance 33" denotes kaempferol3-O-[2-O"-(E)-p-coumaroyl][beta-D-glucopyranosyl-(1→3)-O-alpha-L-rhamnopyranosyl-(1→6)-O-beta-D-glucopyranoside].

In other words, kaempferol3-O-[2-O"-(E)-p-coumaroyl][beta-D-glucopyranosyl-(1→3)-O-alpha-L-rhamnopyranosyl-(1→6)-O-beta-D-glucopyranoside] exhibited an effect of inhibiting the aggregation by 23.0% as compared with the positive control group when the aggregation in the positive control group (denoted by "Pos.Cont.", only beta amyloid was aggregated without compound treatment) was taken as 100%. This result indicates that kaempferol3-O-[2-O"-(E)-p-coumaroyl][beta-D-glucopyranosyl-(1→3)-O-alpha-L-rhamnopyranosyl-(1→6)-O-beta-D-glucopyranoside] exhibits an effect of inhibiting beta amyloid aggregation superior to those of morin (21.4%) and phenol red (6.4%) which are inhibitors known in the prior art. Consequently, the compounds have the usefulness described above and can be thus utilized in various industrial fields related thereto.

[Experimental Example 2] Cumulative Skin Irritation Experiment

Human repeated insult patch tests (HRIPT) were conducted to determine the cumulative skin irritation by kaempferol3-O-[2-O"-(E)-p-coumaroyl][beta-D-glucopyranosyl-(1→3)-O-alpha-L-rhamnopyranosyl-(1→6)-O-beta-D-glucopyranoside] and to calculate the concentration range in which kaempferol3-O-[2-O"-(E)-p-coumaroyl][beta-D-glucopyranosyl-(1→3)-O-alpha-L-rhamnopyranosyl-(1→6)-O-beta-D-glucopyranoside] can be used on the skin.

Specifically, 15 healthy adult subjects were randomly selected, the test compositions (compositions for skin containing an emulsifier, a stabilizer, purified water, and the like in addition to the compound) containing the compound at 0.5 wt %, 1 wt %, and 3 wt % were dropped by 20 μl per chamber (IQ chamber, Epitest Ltd, Finland), and the patch was applied to the right side of the upper back of the subject and then replaced with new one after 24 hours. The skin reaction was examined before and after the patch test while the patch test was conducted three times a week and thus nine times for three weeks in total in this manner, the skin reaction was observed until the 48th hour after removal of the final patch, and the average reactivity was determined.

The results are as presented in the following Table 3.

TABLE 3

| | Number of subjects showed ±, +, or ++ reactivity (unit: persons) | | | | | | | | | |
|---|---|---|---|---|---|---|---|---|---|---|
| Test substance and content | 1st time | 2nd time | 3rd time | 4th time | 5th time | 6th time | 7th time | 8th time | 9th time | Average reactivity |
| Control group | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| Novel substance 33 at 0.5 wt % | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| Novel substance 33 at 1 wt % | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |

TABLE 3-continued

| Test substance and content | 1st time | 2nd time | 3rd time | 4th time | 5th time | 6th time | 7th time | 8th time | 9th time | Average reactivity |
|---|---|---|---|---|---|---|---|---|---|---|
| Novel substance 33 at 3 wt % | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |

Reactivity
−: Negative (no reaction)
±: Suspicious or mild erythema and the like
+: Weak reaction (not accompanied by small vesicula), erythema, papule
++: Moderate reaction (with small vesicula), erythema, papule, vesicula
+++: Strong reaction, bulla reaction
Equation of average reactivity
Average reactivity = [{(sum of values obtained by multiplying the number of subjects who showed reactivity and reaction index)/(total number of subjects × highest score (4 points))} × 100]/Number of tests (9 times)
In the above equation, the reaction index is 0 when the reactivity is −, the reaction index is 1 when the reactivity is ±, the reaction index is 2 when the reactivity is +, the reaction index is 4 when the reactivity is ++.
It is judged as a safe composition when the average reactivity is less than 3.

The skin reaction was judged according to the criteria of the International Contact Dermatitis Research Group (ICDRG). In the above table, "Novel substance 33" denotes kaempferol3-O-[2-O"-(E)-p-coumaroyl][beta-D-glucopyranosyl-(1→3)-O-alpha-L-rhamnopyranosyl-(1→6)-O-beta-D-glucopyranoside]. In other words, the substance exhibited (−) reactivity (no subjects showed ±, +, ++, or +++ reactivity) in all the content ranges. Hence, it can be seen that the substance can be used safely on the skin without cumulative skin irritation.

Specific embodiments of the present specification have been described in detail above, and it will be apparent to those skilled in the art that this specific description is only preferred embodiments and that the scope of the present specification is not limited thereto. Accordingly, the actual scope of the present specification will be defined by the appended claims and their equivalents.

The invention claimed is:

1. A method for manufacturing the compound represented by the following Chemical Formula 1, a pharmaceutically acceptable salt thereof, a hydrate thereof or a solvate thereof comprising fermenting green tea leaves to obtain fermented green tea leaves, and then separating the compound from the fermented green tea leaves.

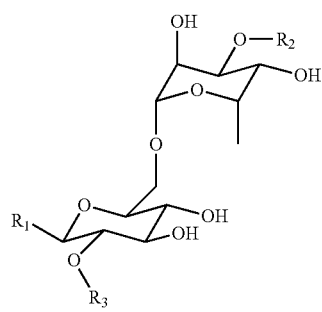

[Chem. 1]

wherein $R_1$ represents $C_{15}H_9O_6$, $R_2$ represents $C_6H_{11}O_5$, and $R_3$ represents $C_9H_7O_2$,
wherein the fermentation is conducted by a post fermentation method.

2. The manufacturing method according to claim 1, wherein $R_1$ denotes a compound represented by the following Chemical Formula 2:

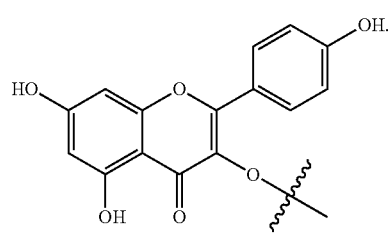

[Chem. 2]

3. The manufacturing method according to claim 1, wherein $R_2$ denotes a compound represented by the following Chemical Formula 3:

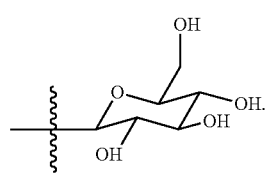

[Chem. 3]

4. The manufacturing method according to claim 1, wherein $R_3$ denotes a compound represented by the following Chemical Formula 4:

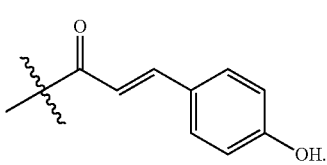

[Chem. 4]

5. The manufacturing method according to claim 1, wherein the compound is kaempferol 3-O-[2O"-(E)-p-coumaroyl][beta-D-glucopyranosyl-(1→3)-O- alpha-L-rhamnopyranosyl-(1→6)-O-beta-D-glucopyranoside].

* * * * *